(12) United States Patent
Mingozzi et al.

(10) Patent No.: US 8,560,088 B2
(45) Date of Patent: Oct. 15, 2013

(54) MEDICAL DEVICE, IN PARTICULAR FOR ELECTROPORATION TREATMENT

(75) Inventors: Franco Mingozzi, Lippo di Calderara di Reno (IT); Alan Dovesi, Bologna (IT); Marco Magni, Ferrara (IT); Mattia Ronchetti, Carpi (IT); Donata Marazzi, Carpi (IT)

(73) Assignee: Citieffe S.R.L., Calderara de Reno (IT)

( * ) Notice: Subject to any disclaimer, the term of this patent is extended or adjusted under 35 U.S.C. 154(b) by 524 days.

(21) Appl. No.: 12/671,410

(22) PCT Filed: Jul. 30, 2007

(86) PCT No.: PCT/IT2007/000545
§ 371 (c)(1),
(2), (4) Date: Jan. 29, 2010

(87) PCT Pub. No.: WO2009/016662
PCT Pub. Date: Feb. 5, 2009

(65) Prior Publication Data
US 2010/0204640 A1 Aug. 12, 2010

(51) Int. Cl.
*A61N 1/18* (2006.01)
(52) U.S. Cl.
USPC .................... 607/145; 607/146; 607/150
(58) Field of Classification Search
USPC .................... 607/145, 146, 150
See application file for complete search history.

(56) References Cited

U.S. PATENT DOCUMENTS

| 279,524 | A | * | 6/1883 | Beaty ........................ 607/145 |
| 5,079,629 | A | | 1/1992 | Oz |
| 5,925,064 | A | | 7/1999 | Meyers et al. |
| 6,208,893 | B1 | | 3/2001 | Hofmann |
| 6,477,410 | B1 | * | 11/2002 | Henley et al. ............... 604/20 |
| 2002/0065480 | A1 | * | 5/2002 | Hofmann ..................... 604/21 |
| 2004/0193211 | A1 | | 9/2004 | Voegele et al. |

FOREIGN PATENT DOCUMENTS

| CN | 1255870 | 6/2000 |
| CN | 1750790 | 3/2006 |
| GB | 2 320 423 A | 6/1998 |
| WO | 99/37358 | 7/1999 |
| WO | 2004/073495 | 9/2004 |

OTHER PUBLICATIONS

International Search Report of PCT/IT2007/000545, dated Jan. 17, 2008.
International Search Report of the International Searching Authority of PCT/IT2007, dated Jan. 17, 2008.
Office Action from China Application No. 200780100816.X, dated Aug. 17, 2012, 19 pages.

* cited by examiner

*Primary Examiner* — Joseph Dietrich
(74) *Attorney, Agent, or Firm* — Hamre, Schumann, Mueller & Larson, P.C.

(57) ABSTRACT

A medical device, in particular for electroporation treatment, characterized by having:
 a thimble-like main body fitted, in use, to a hand of an operator; and
 a member connected to the main body and fitted with needles by which the operator performs the therapeutic treatment.

22 Claims, 6 Drawing Sheets

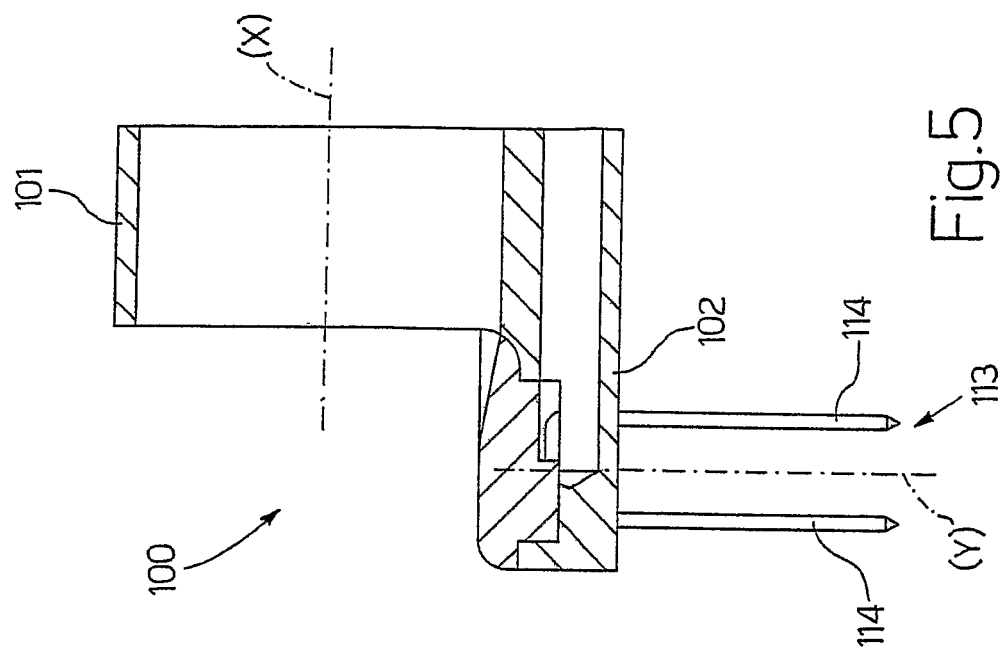
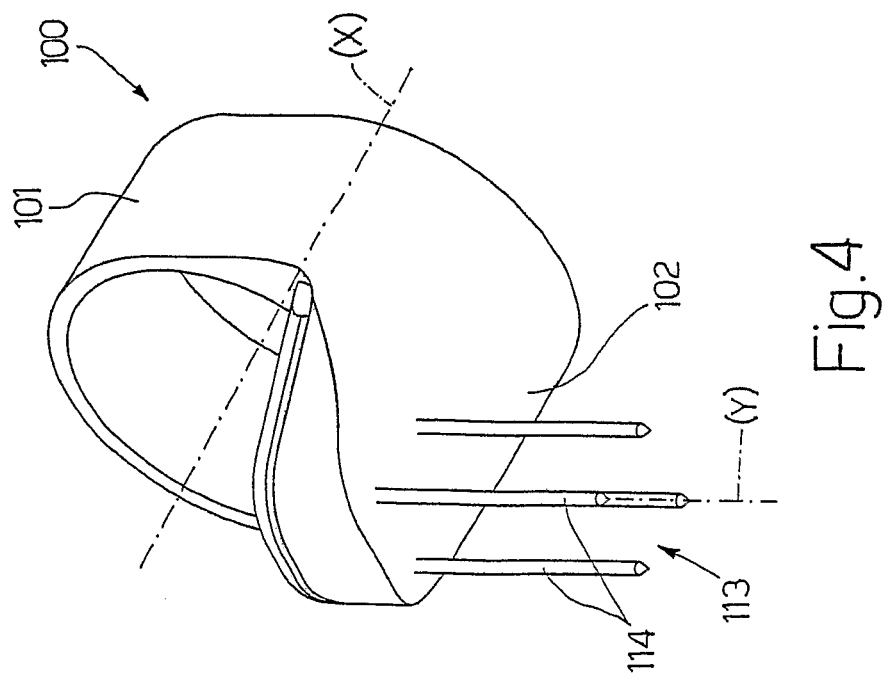
Fig.5
Fig.4

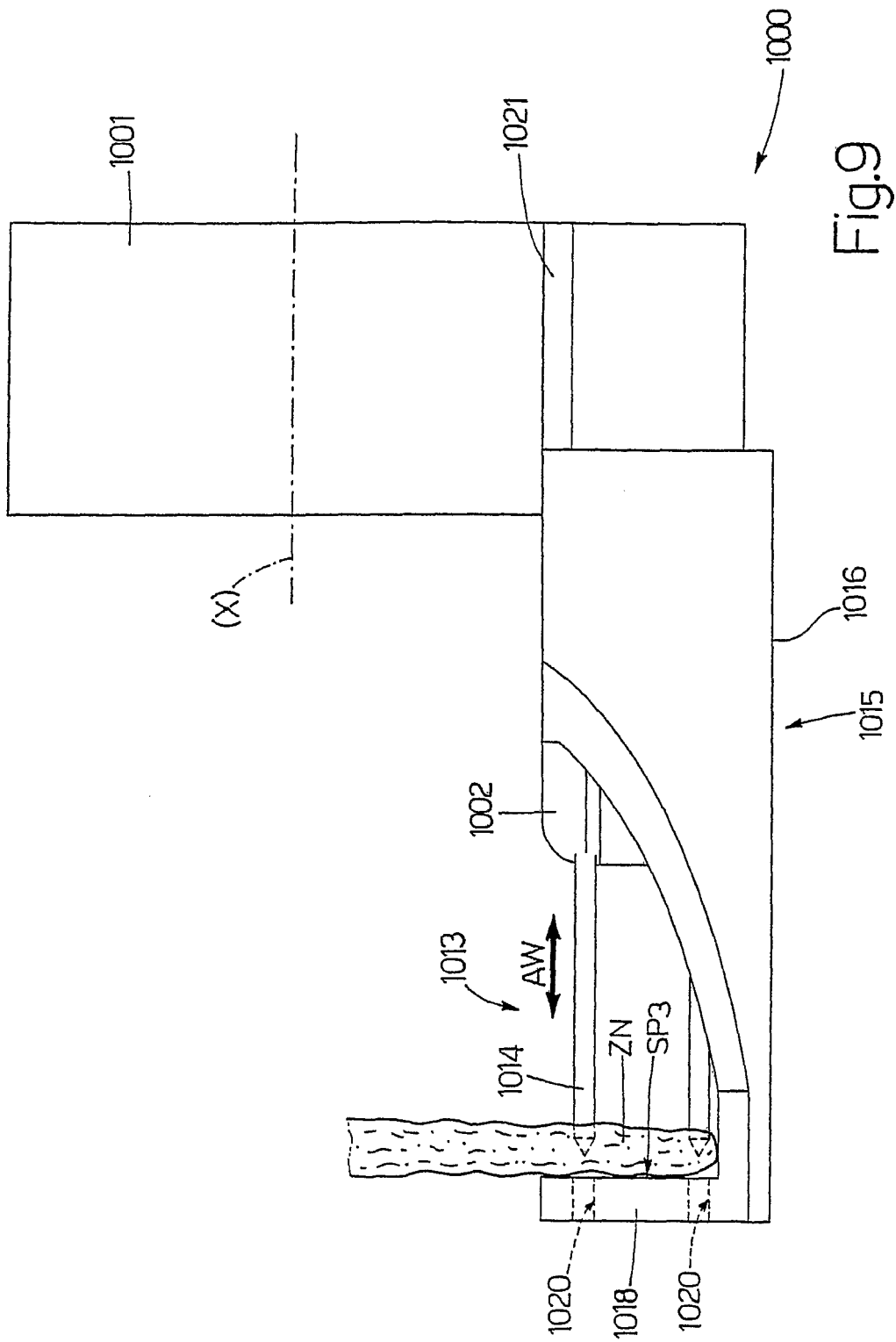

MEDICAL DEVICE, IN PARTICULAR FOR ELECTROPORATION TREATMENT

TECHNICAL FIELD

The present invention relates to a medical device, in particular for electroporation treatment, which is normally a compulsory step in electrochemotherapy treatment in general.

Herein, "electroporation" is intended to mean a physical phenomenon by which to enhance the permeability of cell membranes by means of short, intense electric pulses.

As stated, the medical device according to the present invention may be used to particular advantage, though not exclusively, in electrochemotherapy, to which the following description refers purely by way of example.

BACKGROUND ART

As is known, cell penetration of antitumour drugs can be enhanced considerably by means of electric pulses applied using special needles.

"Electrochemotherapy" is a new technique currently used to locally treat and control cutaneous or subcutaneous tumours.

Electrochemotherapy combines two effects:
administration of small doses of drug (bleomycin or cisplatin); and
electroporation of cell membranes.

Increasing permeability allow non- or poorly permeating drugs or other molecules to penetrate the cytoplasm of cancerous cells to achieve greater effectiveness.

Electrochemotherapy is indicated for primary skin tumours (basal and squamous cell carcinomas), single or in-transit metastasis of melanomas, and cutaneous metastasis of other tumours, regardless of histology.

The latest technology as applied to electrochemotherapy gives particularly good results using electric pulses of 1 Hz or 5 kHz frequency, which reduces the number of muscle contractions induced by electric stimulus, and improves patient treatment tolerance. Moreover, repetition of high-frequency pulses reduces treatment time.

Electric pulses of over 1000 V have also been found to give excellent results in terms of drug absorption.

Patient tolerance is also improved for the following reasons:
minimum side effects, so the treatment can be repeated;
no functional organ impairment and no effect on surrounding healthy tissue;
immediate recovery.

"Electroporation" is normally induced using electrodes connected electrically to equipment for generating pulses of the above frequencies and voltages.

Various types of electrodes have been designed to treat different skin areas, by precise distribution of the applied electric field.

The types of electrodes currently used are:
a plate electrode for surface tumours;
an electrode with parallel rows of needles for small, deep-seated tumours;
an electrode with hexagonally arranged needles for large, deep-seated tumours.

The electrodes are fixed to the distal end of rigid, oblong handsets gripped, in use, by the operator.

Currently used rigid handsets are excellent for treating easily accessible skin tumours, but pose serious problems, substantially on account of their rigid structure, when treating less accessible parts of the body, such as the tongue, palate, gums, the first part of the respiratory system, and accessible cavities.

It is therefore an object of the present invention to provide an alternative to rigid handsets, for use in electroporation treatment. The teachings of the present invention, however, also apply, with obvious variations within the scope of any average technician, to other fields, such as internal microcamera examination of the human body.

A microcamera may also be applied to an electroporation device to permit real-time monitoring of the treatment in progress.

The starting point of the present invention was the realization that an operator's finger, in particular the index finger of the right hand (assuming, of course, the operator is right-handed) represents an exceptional natural "handset", which is versatile, articulated, and sensitive enough for applications necessarily requiring a non-rigid instrument with five degrees of freedom.

An inventive "thimble" was therefore devised, equipped with active means (e.g. needle electrodes), and designed to fit onto the end (tip) phalanx of the operator's finger.

An extremely versatile "tool", comprising the operator's finger and the equipped thimble, is thus obtained, which is able to operate successfully in even the most inaccessible and hidden parts of the patient's body that are difficult, if not impossible, to operate on using conventional handsets.

DISCLOSURE OF INVENTION

It is therefore an object of the present invention to provide a medical device designed to eliminate the aforementioned drawbacks, and which, at the same time, is cheap and easy to produce.

According to the present invention, there is provided a medical device as claimed in the accompanying Claims.

BRIEF DESCRIPTION OF THE DRAWINGS

A non-limiting embodiment of the present invention will be described by way of example with reference to the accompanying drawings, in which:

FIG. 4 shows a view in perspective of a second embodiment of a medical device in accordance with the present invention;

FIG. 5 shows a longitudinal section of the second embodiment in FIG. 4;

FIG. 9 shows one practical application of the medical device in FIGS. 6, 7, 8.

BEST MODE FOR CARRYING OUT THE INVENTION

Figure 1:
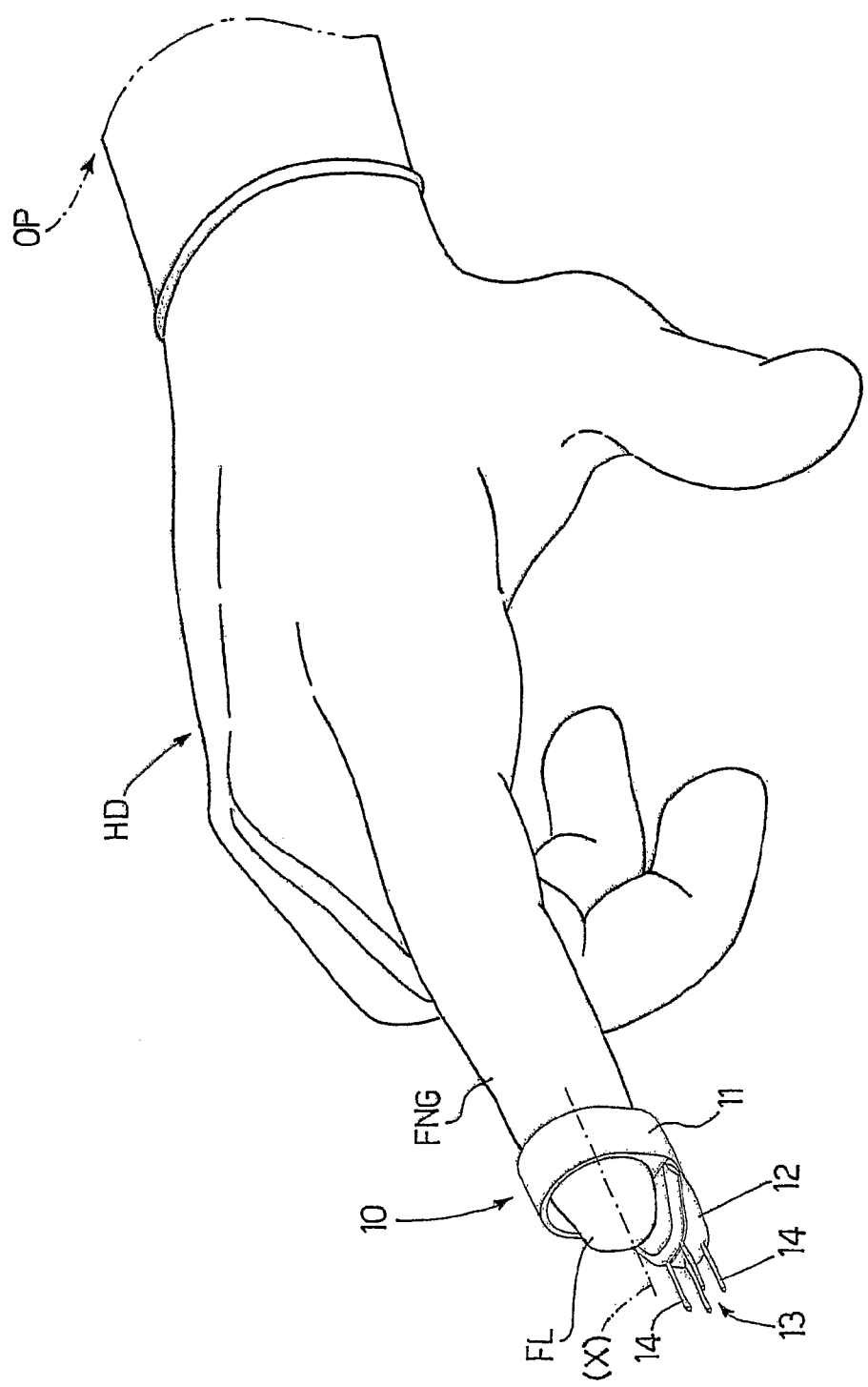
FIG. 1 shows a medical device, in accordance with the present invention, fitted to an operator's hand.
Figure 3:
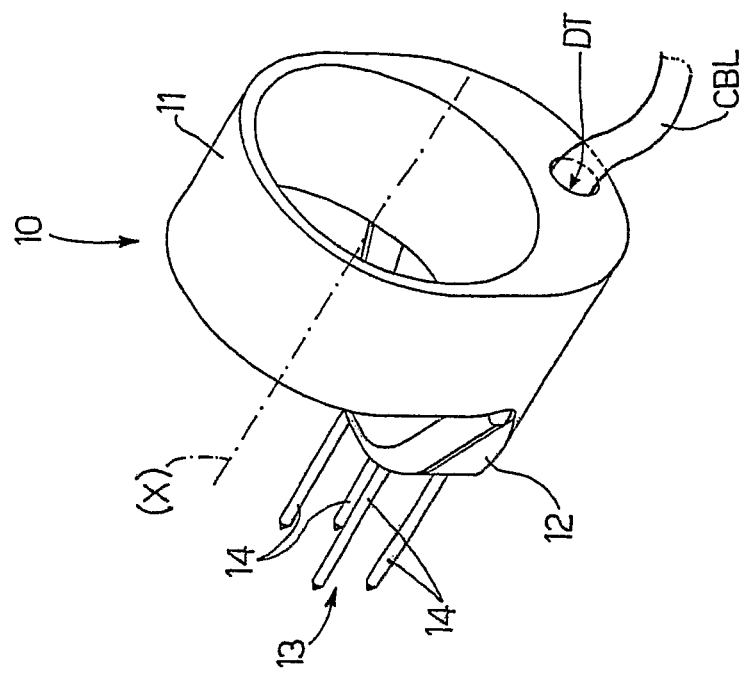
FIG. 3 shows a second view in perspective of the first embodiment in FIG. 2.
Figure 2:
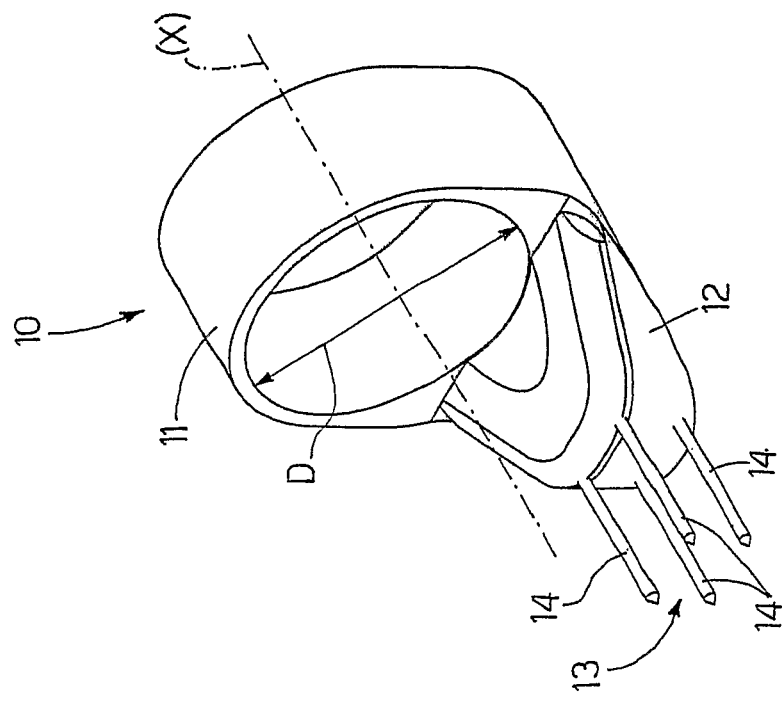
FIG. 2 shows a first view in perspective of a first embodiment of a medical device in accordance with the present invention.
Figure 7:
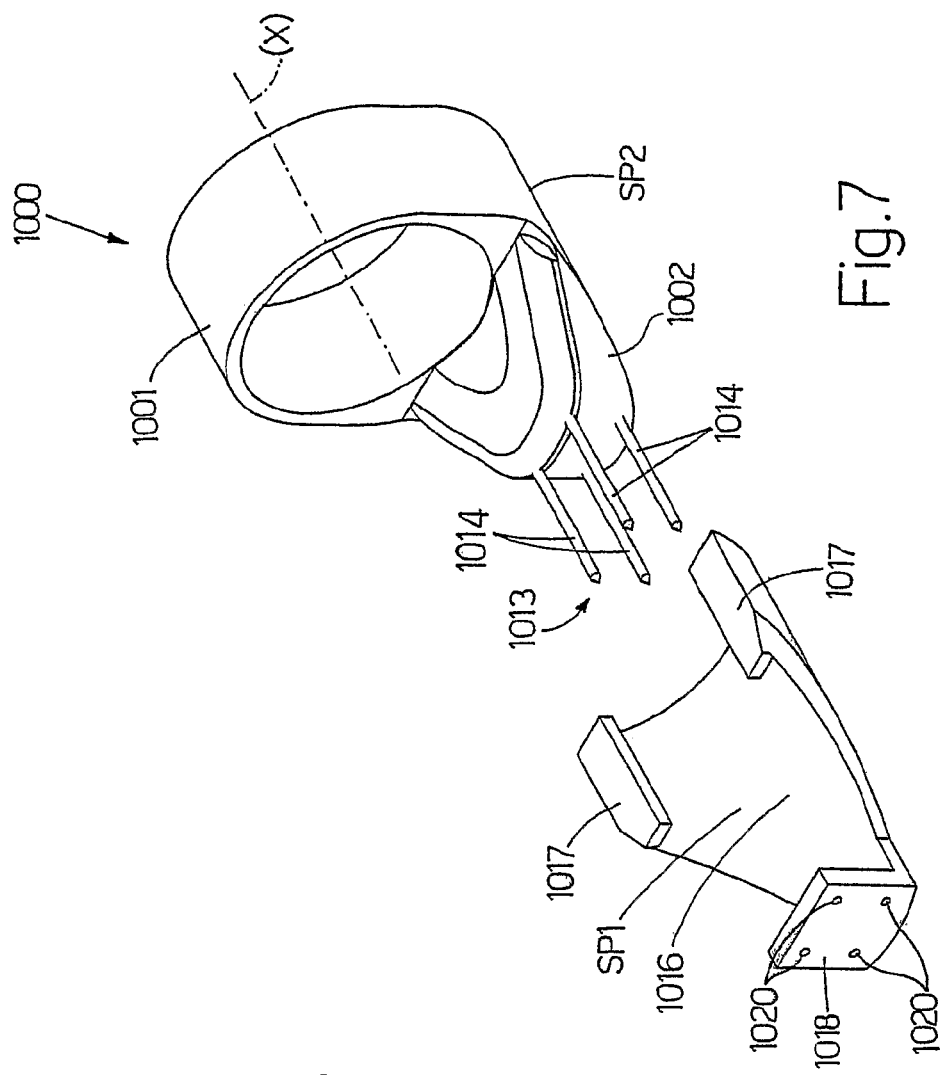
FIG. 7 shows a first exploded view of the medical device in FIG. 6.
Figure 6:
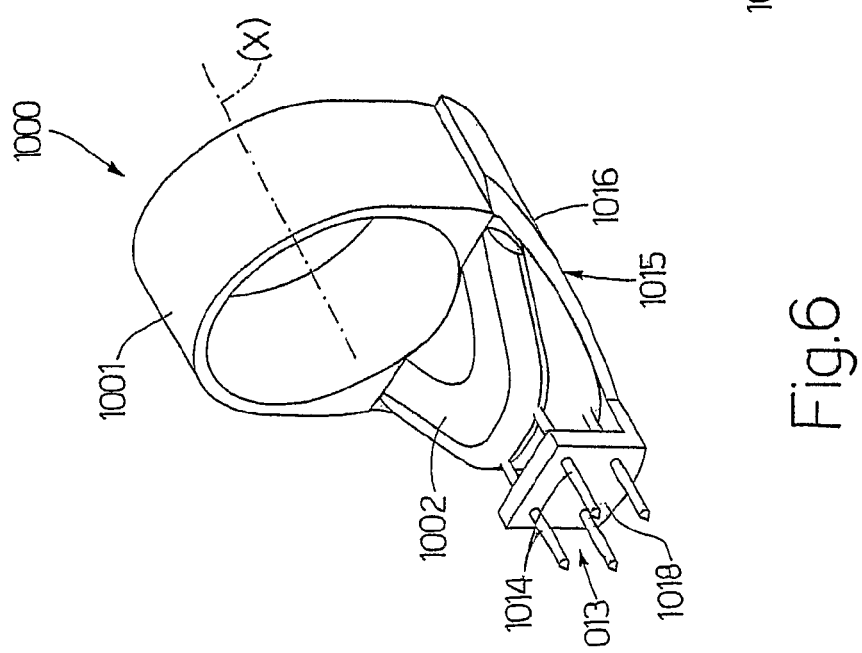
FIG. 6 shows a view in perspective of a third embodiment of a medical device in accordance with the present invention.

Number 10 in FIGS. 1, 2 and 3 indicates as a whole a first embodiment of a medical device in accordance with the present invention.

Medical device 10 comprises a thimble-like main body 11, which is fitted, in use, to a gloved hand HD of an operator OP (not shown). More specifically, in use, main body 11 is worn by the operator OP on the distal (tip) phalanx FL of a finger FNG.

Obviously, if the operator is right-handed, finger FNG is preferably, though not necessarily, the index finger of the right hand.

Medical device 10 also comprises a projecting member 12 (FIGS. 2, 3) projecting from main body 11 and fitted with active means 13 for performing a given therapeutic treatment. In the example shown in FIGS. 1, 2 and 3, active means 13 in turn comprise a number of needles 14 for electroporation treatment.

In the first embodiment of the present invention shown in FIGS. 1, 2 and 3, needles 14 are substantially parallel to an axis (X) of substantial longitudinal symmetry of main body 11.

Projecting member 12 may be either formed in one piece with or glued to main body 11.

Projecting member 12 may also be fitted to main body 11 by a joint.

In an embodiment not shown in the attached drawings, projecting member 12 is hinged to main body 11 to permit angular adjustment of projecting member 12 with respect to main body 11; in which case, fastening means, comprising, for example, a screw, are also provided to lock projecting member 12 in a given angular position with respect to main body 11 to perform a given medical operation.

Both the main body and projecting member 12 are preferably, though not necessarily, made of strong, biocompatible polymer material suitable for manufacturing medical devices.

In another embodiment not shown, main body 11 has means for adjusting its diameter D to adapt main body 11 to the size of the operator's finger. More specifically, in one particularly straightforward solution, main body 11 has at least one through cut dividing it into two, so that diameter D of main body 11 adapts to the diameter of the operator's finger by virtue of the elasticity of the plastic material.

Both main body 11 and projecting member 12 have at least one duct DT for housing the power wires and/or cables of active means 13. More specifically, if active means 13 comprise electroporation needles 14, duct DT houses an electric power cable CBL (FIG. 3). In another embodiment not shown, if active means 13 comprise a microcamera, duct DT houses optical fibres (not shown) for light and/or image transmission.

A thread (not shown) may be attached to main body 11 to recover device 10 in the event of main body 11 slipping accidentally off the finger FNG of the operator OP.

Though projecting member 12 projecting from main body 11 is useful, in an embodiment not shown, active means 13 are fitted directly to main body 11.

FIGS. 4 and 4 show a second embodiment of the present invention.

In this embodiment, a medical device 100 comprises a thimble-like main body 101 attached to a projecting member 102 fitted with active means 113 by which the operator OP performs a given therapeutic treatment.

In this case, the needles 114 defining active means 113 are parallel to an axis (Y) perpendicular to an axis (X) of substantial longitudinal symmetry of main body 101.

All the features described in connection with the FIG. 1, 2, 3 embodiment also apply to medical device 100 in FIGS. 4 and 5.

In an embodiment not shown, a first number of needles are parallel to axis (X), and a second number of needles are perpendicular to axis (X).

FIGS. 6, 7, 8, 9 show a third embodiment of the present invention.

In this, as in the other embodiments described, a medical device 1000 comprises a thimble-like main body 1001, and a projecting member 1002 projecting from main body 1001. And projecting member 1002 is fitted with active means 1013 comprising needles 1014 parallel to an axis (X) of substantial longitudinal symmetry of main body 1001.

In other words, in this embodiment, the spatial arrangement of main body 1001, projecting member 1002, and needles 1014 is the same as in the first embodiment in FIGS. 1, 2 and 3.

As shown in FIGS. 6, 7, 8 and 9, device 1000 also comprises a slide 1015 having a central member 1016 substantially parallel to axis (X) and to which are attached two skids 1017 on opposite sides of axis (X). Slide 1015 also comprises an abutment member 1018 substantially perpendicular to axis (X) and having a number of holes 1020 aligned with needles 1014 projecting from projecting member 1002.

Figure 8:
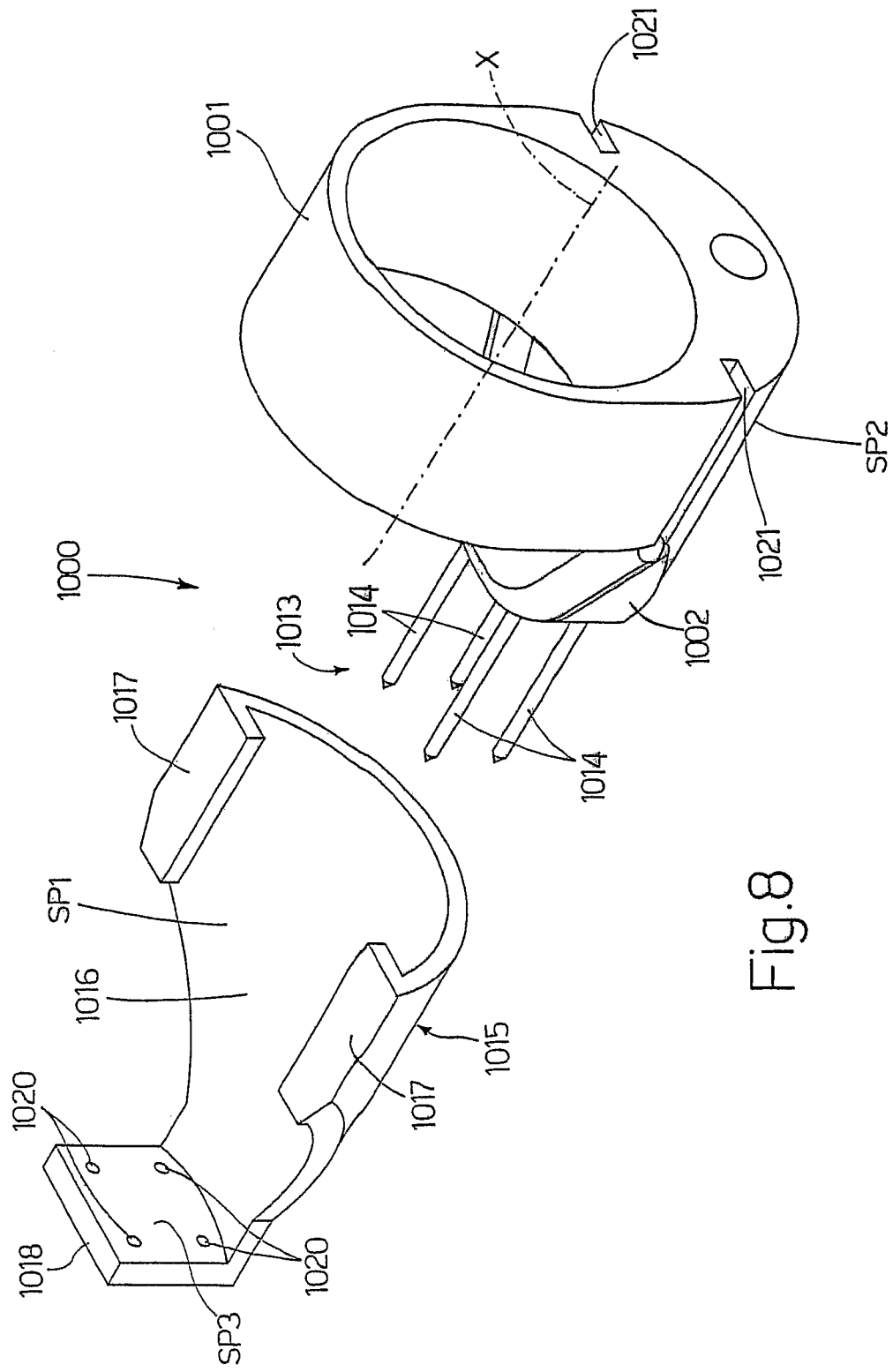
FIG. 8 shows a second exploded view of the medical device in FIG. 6.

In actual use, each skid 1017 engages a respective guide 1021 formed in main body 1001 (FIG. 8). Both guides 1021 are parallel to axis (X), and allow slide 1015 to slide with respect to main body 1001, projecting member 1002, and needles 1014, in the direction of arrow AW (FIG. 9). Moreover, for slide 1015 to slide smoothly, the inner surface SP1 of slide 1015 has substantially the same curvature as the outer surface SP2 of main body 1001 and projecting member 1002.

In actual use, as shown in FIG. 9, when treating an area ZN of particularly soft tissue, the area ZN is inserted between the tips of needles 1014 and an inner surface SP3 of abutment member 1018, which thus acts as an abutment surface for area ZN to assist penetration of area ZN by the tips of needles 1014.

Slide 1015 may obviously be slid onto main body 1001 either manually by the operator OP or by other means not shown.

All the additional features described in connection with the FIG. 1, 2, 3 embodiment and the FIG. 4, 5 embodiment also apply to medical device 1000 in FIGS. 6, 7, 8 and 9.

The main advantage of the medical device described lies in it being extremely versatile, and being able to operate successfully in even the most inaccessible and hidden parts of the patient's body that are difficult, if not impossible, to operate on using conventional rigid handsets.

The invention claimed is:

1. A medical device, comprising:
   a ring-shaped main body configured to be fitted to a hand of an operator;
   a projecting member connected to said main body; and
   a plurality of needles connected to the projecting member, and by which the operator performs a given electroporation therapeutic treatment,
   wherein said needles are substantially parallel to an axis (X) of substantial longitudinal symmetry of said main body, and
   wherein at least one needle is substantially parallel to the axis (X) of substantial longitudinal symmetry of said main body, and at least one needle is substantially parallel to an axis (Y) perpendicular to axis (X).

2. The medical device according to claim 1, wherein said main body is worn by the operator on the distal end (tip phalanx) of a finger.

3. The medical device according to claim 1, wherein said needles are substantially parallel to an axis (Y) perpendicular to an axis (X) of substantial longitudinal symmetry of the main body.

4. The medical device according to claim 1, wherein said projecting member is formed in one piece with the main body.

5. The medical device according to claim 1, wherein said projecting member is glued to said main body.

6. The medical device according to claim 1, wherein said projecting member is connected by a joint to said main body.

7. The medical device according to claim 1, wherein said projecting member is hinged to the main body to permit angular adjustment of the projecting member with respect to the main body.

8. The medical device according to claim 7, further comprising fastening means for locking projecting member in a given angular position with respect to main body.

9. The medical device according to claim 1, wherein both main body and projecting member are made of a polymer material.

10. The medical device according to claim 1, wherein main body has means for adjusting its diameter to adapt main body to the size of the operator's finger.

11. The medical device according to claim 10, wherein main body has at least one through cut dividing main body into two.

12. The medical device according to claim 1, wherein main body and projecting member have at least one duct for housing power wires and/or cables for the needles.

13. The medical device according to claim 1, further comprising a microcamera connected to the projecting member.

14. The medical device according to claim 12, wherein the duct houses optical fibres for light and/or image transmission.

15. The medical device according to claim 12, wherein main body is attached to a thread to recover the device in the event of main body slipping accidentally off the finger of the operator.

16. A method for using the medical device according to claim 1, comprising:
wearing the ring-shaped main body of the medical device on a finger of the operator; and
penetrating an area of soft tissue with tips of the needles.

17. The method according to claim 16, further comprising:
performing electroporation treatment to the area of the soft tissue with the tips of the needles.

18. The method according to claim 16, further comprising:
performing electrochemotherapy treatment to the area of the soft tissue with the tips of the needles.

19. A medical device, comprising:
a ring-shaped main body configured to be fitted to a hand of an operator,
a projecting member connected to said main body;
a plurality of needles connected to the projecting member, and by which the operator performs a given electroporation therapeutic treatment; and
a slide having a central member to which are attached two skids, each of the skids engages a respective guide formed in said main body, each of the guides permitting translation of said slide with respect to said main body, wherein an inner surface of said slide has substantially same curvature as an outer surface of said main body.

20. The medical device according to claim 19, further comprising:
said needles are substantially parallel to an axis (X) of substantial longitudinal symmetry of said main body; and
said slide having an abutment member substantially perpendicular to an axis (X), the abutment member including needle holes for receiving the needles.

21. The medical device according to claim 20, wherein said abutment member is configured to receive soft tissue between tips of said needles and an inner surface of said abutment member to assist penetration of the soft tissue by said needles.

22. A method for using the medical device according to claim 20, comprising:
wearing the ring-shaped main body of the medical device on a finger of the operator;
inserting an area of soft tissue between tips of the needles and an inner surface of the abutment member;
penetrating the area with the tips of the needles; and
performing electroporation treatment via the needles.

* * * * *

UNITED STATES PATENT AND TRADEMARK OFFICE
CERTIFICATE OF CORRECTION

| | | |
|---|---|---|
| PATENT NO. | : 8,560,088 B2 | Page 1 of 1 |
| APPLICATION NO. | : 12/671410 | |
| DATED | : October 15, 2013 | |
| INVENTOR(S) | : Mingozzi et al. | |

It is certified that error appears in the above-identified patent and that said Letters Patent is hereby corrected as shown below:

On the title page, item 73, after "S.R.L.": delete "Calderara de Reno" and insert --Calderara di Reno--.

Signed and Sealed this
Seventeenth Day of June, 2014

Michelle K. Lee
*Deputy Director of the United States Patent and Trademark Office*